United States Patent
Bennett

(10) Patent No.: US 11,039,842 B1
(45) Date of Patent: Jun. 22, 2021

(54) SURGICAL DRILL BIT HAVING DUAL CUTTING ELEMENTS WITH OPPOSITE HAND ROTATION

(71) Applicants: Smith & Nephew, Inc., Memphis, TN (US); Smith & Nephew Pte. Limited, Singapore (SG); Smith & Nephew Orthopaedics AG, Baar (CH)

(72) Inventor: Charles Ramsey Bennett, Memphis, TN (US)

(73) Assignees: Smith & Nephew, Inc., Memphis, TN (US); Smith & Nephew Pte. Limited, Singapore (SG); Smith & Nephew Orthopaedics AG, Zug (CH)

( * ) Notice: Subject to any disclaimer, the term of this patent is extended or adjusted under 35 U.S.C. 154(b) by 41 days.

(21) Appl. No.: 16/660,005

(22) Filed: Oct. 22, 2019

Related U.S. Application Data

(60) Provisional application No. 62/751,864, filed on Oct. 29, 2018.

(51) Int. Cl.
*A61B 17/16* (2006.01)

(52) U.S. Cl.
CPC ........ *A61B 17/1615* (2013.01); *A61B 17/164* (2013.01)

(58) Field of Classification Search
CPC . A61B 17/16; A61B 17/1613; A61B 17/1615; A61B 17/1617; A61B 17/162
See application file for complete search history.

(56) References Cited

U.S. PATENT DOCUMENTS

| | | | | |
|---|---|---|---|---|
| 4,632,100 A | * | 12/1986 | Somers | A61B 17/16 606/232 |
| 4,978,350 A | * | 12/1990 | Wagenknecht | A61B 17/8635 411/387.7 |
| 6,197,031 B1 | * | 3/2001 | Barrette | A61B 17/155 606/311 |
| 6,312,432 B1 | * | 11/2001 | Leppelmeier | A61B 17/1615 408/225 |

(Continued)

OTHER PUBLICATIONS

Zimmer® MotionLoc® Screw for the Periarticular Locking Plate System, Surgical Technique, p. 1-8, www.zimmer.com (2015).

(Continued)

*Primary Examiner* — Eric S Gibson
(74) *Attorney, Agent, or Firm* — Kacvinsky Daisak Bluni PLLC

(57) ABSTRACT

A surgical drill bit and corresponding systems and methods of use are disclosed. The surgical drill bit being adapted and configured for cutting first and second, collinear holes within first and second portions of a patient's bone. In one embodiment, the drill bit includes a smaller diameter distal cutting portion, a larger diameter proximal cutting portion, and a shoulder positioned between the smaller diameter distal cutting portion and the larger diameter proximal cutting portion. In use, the smaller diameter distal cutting portion is adapted and configured to cut when rotated in a first direction, the larger diameter proximal cutting portion is adapted and configured to cut when rotated in a second, opposite direction. In this manner, over-drilling of the patient's bone is thereby prevented.

10 Claims, 14 Drawing Sheets

(56) References Cited

U.S. PATENT DOCUMENTS

| | | | |
|---|---|---|---|
| 8,226,654 B2* | 7/2012 | Ranck | A61C 8/0089 |
| | | | 606/80 |
| 9,089,346 B2 | 7/2015 | Schoutens | |
| 9,763,712 B2 | 9/2017 | Appenzeller et al. | |
| 10,610,243 B2* | 4/2020 | Sommers | A61B 17/72 |
| 10,792,053 B2* | 10/2020 | Asfora | A61B 17/1757 |
| 2003/0018337 A1* | 1/2003 | Davis | A61B 17/1655 |
| | | | 606/80 |
| 2005/0149031 A1* | 7/2005 | Ciccone | A61B 17/864 |
| | | | 606/280 |
| 2010/0145341 A1* | 6/2010 | Ranck | A61B 17/1615 |
| | | | 606/80 |
| 2011/0015634 A1* | 1/2011 | Smith | A61B 17/164 |
| | | | 606/80 |
| 2011/0112540 A1 | 5/2011 | McLean et al. | |
| 2013/0261628 A1* | 10/2013 | Burley | A61B 17/1615 |
| | | | 606/80 |
| 2013/0296864 A1* | 11/2013 | Burley | A61B 17/17 |
| | | | 606/80 |
| 2014/0113245 A1* | 4/2014 | Heo | A61C 1/084 |
| | | | 433/75 |
| 2015/0342617 A1* | 12/2015 | Kunz | A61C 1/14 |
| | | | 433/75 |
| 2019/0105060 A1* | 4/2019 | Sommers | A61B 17/72 |
| 2019/0125371 A1* | 5/2019 | Asfora | A61B 17/864 |
| 2019/0290299 A1* | 9/2019 | Pacaccio | A61B 17/8625 |
| 2019/0298392 A1* | 10/2019 | Capote | A61B 17/1615 |
| 2020/0330107 A1* | 10/2020 | Sommers | A61B 17/72 |
| 2020/0353543 A1* | 11/2020 | Laird | A61B 17/1615 |
| 2020/0360008 A1* | 11/2020 | Breslich | A61B 17/17 |

OTHER PUBLICATIONS

REDAPT™ Revision Femoral System, Surgical Technique, Smith & Nephew, Inc., p. 1-30, www.smith-nephew.com (2016).

Dynamic Locking Screw (DLS) System. For use with locking compression plate (LCP) systems, Technique Guide, p. 1-20, www.synthes.com (2011).

* cited by examiner

SURGICAL DRILL BIT HAVING DUAL CUTTING ELEMENTS WITH OPPOSITE HAND ROTATION

CROSS-REFERENCE TO RELATED APPLICATION

This application claims the benefit of U.S. Provisional Patent Application No. 62/751,864, filed Oct. 29, 2018, entitled "Surgical Drill Bit Having Dual Cutting Elements with Opposite Hand Rotation," the entire contents of which application is hereby incorporated by reference in its entirety.

FIELD OF THE DISCLOSURE

The present disclosure relates generally to orthopedic devices, systems, and methods for facilitating fracture fixation, and particularly to a drill bit and associated systems and methods for forming collinear holes having variable diameters.

BACKGROUND OF THE DISCLOSURE

People suffer bone fractures each year. Bone fractures are often repaired by implanting a bone fixation implant such as, for example, a bone plate, an intramedullary nail, a humeral stem, or the like, into and/or across the fracture site. Depending upon which bone is to be treated, the bone fixation implant may be provided in any shape and size as required.

As will be appreciated by one of ordinary skill in the art, during a surgical procedure for inserting a bone fixation implant, a surgeon's visibility of the implantation site might be compromised. As a result, there is a risk during formation of one or more holes in a patient's bone that the bone may be over-drilled. For example, during formation of one or more holes in a first portion of a patient's bone, the drill bit may be inserted too far thus piercing a second portion of the patient's bone.

Moreover, in some procedures, first and second collinear holes are required in first and second portions of a patient's bone. For a variety of reasons, it may be desirable to provide the first and second collinear holes with varying diameters. However, forming first and second collinear holes with varying diameters in first and second portions of a patient's bone may require multiple drill bits, which requires multiple steps, which increases the chances that the holes may become non-collinear, over-drilled, etc.

Thus, it would be beneficial to provide an easy to use apparatus, system, and method that facilitates the formation of collinear first and second holes in a patient's bone where the first hole has a larger diameter than the second hole. Additionally, it would be beneficial to eliminate, or at least minimize, the risk of over-drilling of the first and second holes. Furthermore, it would be beneficial to enable a surgical procedure that eliminates the need for multiple steps and components associated with current procedures. Additionally, in connection with, for example, implantation of a bone plate, it would be beneficial to enable a surgical procedure that allows micro-motion between the bone plate and the patient's bone, but which does not require the introduction of new specialized medical implants or systems.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a drill bit having varying diameters to enable a surgeon to create first and second collinear holes in first and second portions of a patient's bone while preventing, or at least minimizing, the risk of over-drilling.

In one embodiment, a surgical drill bit adapted and configured for forming, cutting, etc. one or more holes within a patient's bone is disclosed. The drill bit may include a smaller diameter distal cutting portion, a larger diameter proximal cutting portion spaced from the distal cutting portion, and a shoulder positioned between the smaller diameter distal cutting portion and the larger diameter proximal cutting portion. In use, the smaller diameter distal cutting portion is adapted and configured to cut when rotated in a first direction, the larger diameter proximal cutting portion is adapted and configured to cut when rotated in a second, opposite direction.

In another embodiment, a surgical drill bit adapted and configured for forming, cutting, etc. one or more holes within a patient's bone is disclosed. The drill bit may include an elongated cylindrical body portion having a longitudinal axis and a distal cutting portion including and one or more cutting elements that wind about the longitudinal axis in a first direction. The body portion includes a second cutting portion spaced from the distal cutting portion, the second cutting portion including one or more cutting elements positioned proximal of the distal cutting portion, the one or more cutting elements formed on the body portion winding about the longitudinal axis in a second direction, the second direction being opposite the first direction.

In one embodiment, the distal cutting portion includes a first diameter and the second cutting portion formed on the body portion includes a second diameter, the second diameter being larger than the first diameter.

In one embodiment, the drill bit further includes a shoulder positioned between the distal cutting portion and the second cutting portion formed on the body portion.

In one embodiment, the one or more cutting elements formed on the body portion extend from a distal end of the body portion towards a proximal end of the body portion (e.g., the one or more cutting elements of the distal cutting portion extend from a distal end of the body portion towards a proximal end of the body portion). The one or more cutting elements formed on the second or proximal cutting portion extend from an origination point spaced a distance from a termination point of the one or more cutting elements of the distal cutting portion towards the proximal end of the body portion.

In one embodiment, a proximal end of the body portion includes an engagement portion configured to be coupled to a drill.

In one embodiment, a distal end of the distal cutting portion includes a self-cutting tip.

In one embodiment, a surgical kit including one or more bone fixation implants (e.g., bone plates, IM Nail, etc.), one or more bone screws, and one or more surgical drill bits in accordance with the drill bit described herein may be provided.

In one embodiment, the drill bit may be used to drill first and second collinear holes in the near and far cortex of a patient's bone, respectively. In use, the first and second holes have varying diameters. As such, the second hole formed in the far cortex of the patient's bone may have a first diameter appropriately sized for receiving, for example, a conventional locking screw while the first hole formed in the near cortex of the patient's bone may have a second, larger diameter be arranged and configured to, for example, create a specified amount of clearance at the near cortex to allow controlled micro-motion at the fracture sight to induce interfragmentary motion.

In one embodiment a method of forming a hole in a patient's bone is disclosed. The method includes cutting a hole in a first cortex of the patient's bone using a drill bit having a first diameter distal cutting portion; contacting the first cortex with a shoulder formed on the drill bit; reversing a direction of rotation of the drill bit; enlarging the hole formed in the first cortex of the patient's bone using a second diameter proximal cutting portion formed on the drill bit; contacting a second cortex of the patient's bone with the first diameter distal cutting portion; reversing the direction of rotation of the drill bit; and cutting a hole in the second cortex of the patient's bone using the first diameter distal cutting portion of the drill bit.

In one embodiment, the second diameter proximal cutting portion has a larger diameter than the first diameter distal cutting portion.

Embodiments of the present disclosure provide numerous advantages. For example, use of the drill bit of the present disclosure enables a user to drill multiple, collinear holes having varying diameters with a single drill bit. As a result, a simplified surgical procedure is created that ensures the collinearity of the holes while reducing the risk of over drilling (e.g., drill bit prevents, or at least reduces, the possibility of over-drilling the holes formed in the patient's bone). In one embodiment, the drill bit provides an easy to use apparatus and method for drilling a larger diameter hole in the near cortex of a patient's bone and a smaller diameter hole in the far cortex of the patient's bone without requiring multiple drill bits and the corresponding removing and reinserting of drill bits. As a result, collinearity of the holes formed in the near and far cortex is ensured. Additionally, the drill bit prevents accidental over-drilling of the far cortex. Additionally, in connection with, for example, implantation of bone plates, the use of the drill bit augments standard locking plating practices rather than relying on novel medical implants.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
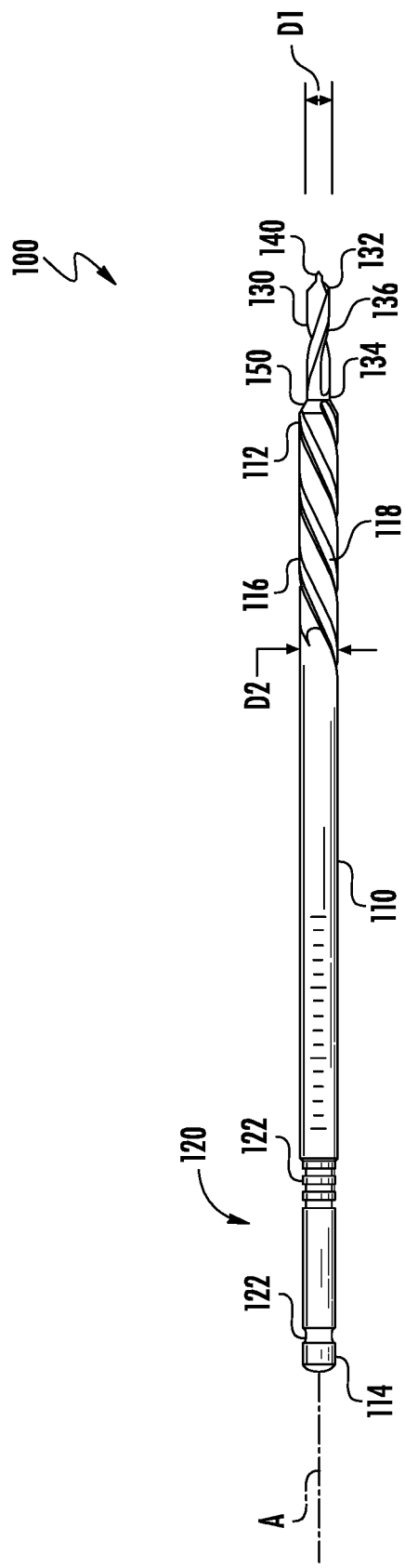
FIG. 1 shows a top view of an example embodiment of a drill bit in accordance with the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

DETAILED DESCRIPTION

Embodiments of an improved apparatus for a drill bit along with corresponding systems and methods of use in accordance with the present disclosure will now be described more fully hereinafter with reference to the accompanying drawings, in which preferred embodiments of the present disclosure are presented. As will be described and illustrated, in some embodiments, the improved apparatus includes a stepped drill bit having a smaller diameter distal cutting portion and a larger diameter proximal cutting portion. The smaller diameter distal cutting portion being adapted and configured to cut or advance when rotated in a first direction while the larger diameter proximal cutting portion is adapted and configured to cut or advance when rotated in a second, opposite direction. A shoulder or a stop is provided between the smaller diameter distal cutting portion and the larger diameter proximal cutting portion. In use, the combination of providing a distal cutting portion that cuts when rotated in a first direction, a proximal cutting portion that cuts when rotated in a second direction, and a shoulder acts to prevent further advancement of the drill bit without reversing rotation of the drill bit. As a result, the device provides, inter alia, risk mitigation to prevent over-drilling a patient's bone. That is, for example, in one embodiment, the device enables a user to drill multiple collinear holes of varying diameters with one drill bit thus providing a simpler and abbreviated surgical procedure that reduces the risk of over drilling. The drill bit and corresponding methods of the present disclosure may, however, be embodied in many different forms and should not be construed as being limited to the embodiments set forth herein. Rather, these embodiments are provided so that this disclosure will convey certain example embodiments of the apparatus and method to those skilled in the art. In the drawings, like numbers refer to like elements throughout unless otherwise noted.

As will be described in greater detail below, in various embodiments, the improved drill bit and corresponding systems and methods of use provide an easy to use apparatus, system and method for drilling or forming a larger diameter hole in a first portion of a patient's bone such as, for example, the near cortex of a patient's bone and a smaller diameter hole in a second portion of the patient's bone such as, for example, the far cortex of the patient's bone without requiring multiple drill bits and the corresponding removing and reinserting of drill bits In use, the improved drill bit and corresponding systems and methods of use according to the present disclosure may be used in connection with any bone fixation implant (e.g., bone plate, intramedullary nail, humeral stem, etc.) now known or hereafter developed. As such, the present disclosure has widespread applicability and should not be limited.

Referring to FIG. 1, a non-limiting example embodiment of a surgical drill bit 100 is illustrated. In use, the drill bit 100 is configured to form a hole in an anatomical structure such as, for example, a patient's bone. As illustrated, the drill bit 100 includes an elongated cylindrical body portion 110 and a distal cutting portion 130. In use, the drill bit 100 is configured to form or otherwise cut first and second collinear holes into a patient's bone, the first and second holes having varying diameters.

In use, the distal cutting portion 130 is configured to form or otherwise cut a first hole in a patient's bone. As illustrated, the distal cutting portion 130 includes a distal end 132 and a proximal end 134 spaced from the distal end 132 along a longitudinal direction of the drill bit 100. The distal end 132 of the distal cutting portion 130 defines a cutting tip 140. As will be appreciated by one of ordinary skill in the art, the distal cutting portion 130 may include one or more cutting elements, helical flutes, cutting geometries, abrasive edges such as, for example, a rasp, or knurling, or the like 136 (used interchangeably herein without the intent to limit) that wind about a longitudinal axis A of the drill bit 100 from the distal end 132 to the proximal end 134 of the distal cutting tip 130. As illustrated, in one example embodiment, the flutes 136 wind about the longitudinal axis of the drill bit 100 in a first (e.g., clockwise) direction, although it is envisioned that the first direction may be a counter-clockwise direction. In this manner, in use, the distal cutting portion 130 operates to cut or advance (e.g., form a hole in the patient's bone) when rotated in the first direction only (e.g., distal cutting portion 130 does not cut or advance when rotated in a second, opposite direction).

While the distal cutting portion 130 is illustrated as including two helical flutes 136 it should be appreciated that the distal cutting portion 130 can include any number of flutes 136 as desired. For example, the distal cutting portion 130 can include three, four, or more flutes 136. The flutes 136 can be substantially identical to each other as illustrated, or the flutes 136 can be different from each other.

In use, the body portion 110 is configured to form or otherwise cut a second hole in a patient's bone. As illustrated, the body portion 110 includes a distal end 112 and a proximal end 114 spaced from the distal end 112 along a longitudinal direction of the drill bit 100. The proximal end 114 of the body portion 110 may include an engagement portion 120 configured to be coupled to a drill, handle, etc. The engagement portion 120 is configured to allow the drill bit 100 to be coupled to, for example, a drill (e.g., powered or manual). As shown, the engagement portion 120 can include one or more surfaces 122 that are configured to be gripped by a coupling feature of the drill. It should be appreciated, however, that the engagement portion 120 can have other shapes and can include other features that are configured to be gripped by the drill. For example, the engagement portion 120 can include a partial hexagon shape.

As illustrated, the body portion 110 includes a cutting portion 116 including one or more flutes 118 that wind about the longitudinal axis A of the drill bit 100. The flutes 118 extending from the distal end 112 of the body portion 110 towards the proximal end 114. As illustrated, the flutes 118 may extend a portion of the length thereof. Alternatively, the flutes 118 may extend an entire length of the body portion 110. As illustrated, in one example embodiment, the flutes 118 wind about the longitudinal axis of the drill bit 100 in a second (e.g., counter-clockwise) direction, although it is envisioned that the second direction may be a clockwise direction. In this manner, in use, the cutting portion 116 formed on the body portion 110 operates to cut or advance (e.g., form a hole in the patient's bone) when rotated in the second direction only, which is opposite of the first direction of the distal cutting portion 130 (e.g., the cutting portion 116 formed on the body portion 110 does not cut or advance when rotated in the first direction (i.e., the cutting portion 116 formed on the body portion 110 does not cut or advance when rotated in the same direction as required for the distal cutting portion 130 to cut and/or advance).

While the body portion 110 is illustrated as including two helical flutes 118 it should be appreciated that the body portion 110 can include any number of flutes 118. For example, the body portion 110 can include three, four, or more flutes 118. The flutes 118 can be substantially identical to each other as illustrated, or the flutes 118 can be different from each other.

As illustrated, in one embodiment, the distal cutting portion 130 may include a first diameter D1 and the body portion 110 may include a second diameter D2, wherein the second diameter D2 of the body portion 110 is larger than the first diameter D1 of the distal cutting portion 130 so that a shoulder or a stop (collectively used herein without the intent to limit) 150 is formed, for example, at the junction between the proximal end 134 of the distal cutting portion 130 and the distal end 112 of the body portion 110. As illustrated, in one embodiment, the shoulder 150 may include an angled, sloped, or the like surface for transitioning from the first diameter D1 of the distal cutting portion 130 to the second, larger diameter D2 of the cutting portion 116 formed on the body portion 110. In alternate embodiment, the shoulder 150 may be adapted and configured to provide tactile feedback to the user indicating when to stop advancing the drill bit.

As a result, by incorporating a first distal cutting portion 130 having a first cutting direction, a larger diameter proximal cutting portion 116 having a second cutting direction, and a shoulder 150 positioned between the first distal cutting portion 130 and the larger diameter proximal cutting portion 116, a surgeon can initially cut or form a hole through a first portion a patient's bone such as, for example, the near cortex of a patient's bone, using the distal cutting portion 130. Thereafter, the surgeon can enlarge the hole formed in the first portion of the patient's bone (e.g., near cortex) using the larger diameter proximal cutting portion 116. The surgeon can also cut or form a hole through a second portion of the patient's bone such as, for example, the far cortex of the patient's bone, using the first distal cutting portion 130.

In this manner, the drill bit 100 allows a surgeon to create a larger diameter first hole in a first portion of the patient's bone (e.g., near cortex), the first hole being sized and configured to correspond with the second, larger diameter D2 of the cutting portion 116 formed on the body portion 110. In addition, the drill bit 100 allows a surgeon to create a second hole in a second portion of the patient's bone (e.g., far cortex), the second hole being sized and configured to correspond with the first diameter D1 of the distal cutting portion 130.

Referring to FIGS. 2A-2H, an example method of using the drill bit 100 in connection with implantation of a bone plate 210 will be described and illustrated. In one illustrated method of use, the drill bit 100 is utilized to provide far cortical locking and to enable a specified amount of clearance or space between the hole formed in the near cortex of the patient's bone and the shaft portion of the implanted bone screw thus allowing for controlled micro-motion/interfragmentary motion.

As will be appreciated by one of ordinary skill in the art, a bone plate may be secured across a fracture site. In one common procedure, locking screws may be utilized to engage the bone plate to prevent backing-out of the bone screws (e.g., the bone screw may be secured to the bone plate via threads formed in the head of the bone screw that cooperate with threads formed in the openings formed in the bone plate). In use, this procedure secures the bone plate to the patient's bone and provides a rigid construct between the bone plate and the patient's bone. That is, because the head of the bone screw interdigitates with threads formed in the opening of the bone plate, the bone plate and the bone screws form a rigid or stiff system or construct.

One known disadvantage with such bone plating systems is the increased rate of nonunion or improper bone healing. One common belief is that the increased rate of nonunion is due, in part, to the rigidity or stiffness of the bone plating system or construct. That is, bone fractures routinely rely on secondary bone healing, which relies on interfragmentary motion. However, bone plating systems of this type are rigid and thus prevent movement of the patient's bone fragments.

One solution has been to introduce micro-motion (e.g., flexible or dynamic fixation) into the bone fixation system. It is generally believed that by providing controlled micro-motion or flexibility into the system, advantages are achieved by reducing the amount of stress generally associated with rigid fixation. One approach to introduce micro-motion into the bone plating construct has been to rely on far cortical locking. Far cortical locking facilitates micro-motion at the near cortex (e.g., bone surface adjacent to the bone plate) while maintaining purchase in the far cortex (e.g., bone surface opposite the bone plate).

One known procedure for facilitating far cortical locking includes drilling two holes across the diaphysis of a patient's bone. In a first step, a hole is drilled using a first diameter drill bit through the near cortex of the patient's bone and into the far cortex of the patient's bone. Next, the hole formed in the near cortex of the patient's bone is drilled or enlarged using a second, larger diameter drill bit. By re-drilling the hole in the near cortex with the second, larger diameter drill bit, additional clearance is provided between the resulting bone screw inserted into the hole formed in the near cortex, the additional clearance facilitating micro-motion.

One disadvantage of the current procedure is that it requires two separate drill bits—a first drill bit for forming the initial hole through the near and far cortex of the patient's bone and a second drill bit for enlarging the hole formed in the near cortex. In addition, use of the second drill bit to enlarge the hole in the near cortex introduces the risk that the second drill bit could be advanced too far and into contact with the hole formed in the far cortex, causing unwanted over-drilling of the hole in the far cortex (e.g., enlargement of the hole in the far cortex). Moreover, issues surrounding removing and reintroducing drill bits can also lead to unwarranted non-collinearity between the holes formed in the near and far cortexes.

In contrast to known surgical procedures, utilization of the drill bit 100 in accordance with the present disclosure enables the surgeon to form first and second collinear holes in the patient's near and far cortex, without the risk of over-drilling. Additionally, by forming a larger diameter hole in the near cortex, the device and method enables micro-motion between the implanted bone plate and bone along the near cortex of the patient's bone thus facilitating secondary healing.

Figure 2A:
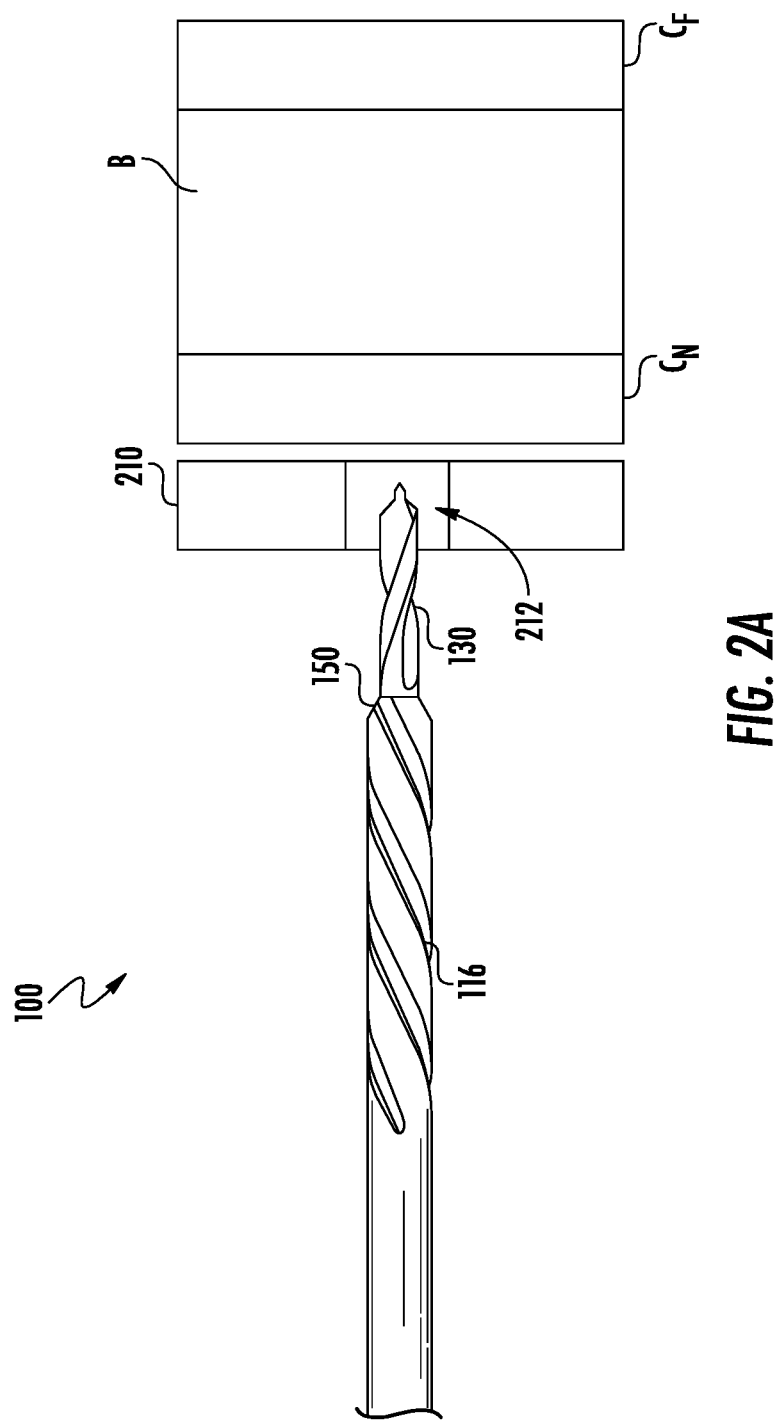
FIGS. 2A-2H shows a series of steps illustrating one example embodiment of a method for using the drill bit shown in FIG. 1.

Referring to FIGS. 2A-2H, an example method of use utilizing the drill bit 100 in connection with implantation of a bone plate 210 will now be described and illustrated. As illustrated in FIG. 2A, the surgeon places the drill bit 100 adjacent to a targeted location in the patient's bone B. In use, as illustrated, the drill bit 100 can be, for example, inserted through an opening 212 formed in a bone plate 210 lying against the patient's bone B. Additionally, and/or alternatively, a drill guide could be incorporated.

Figure 2B:
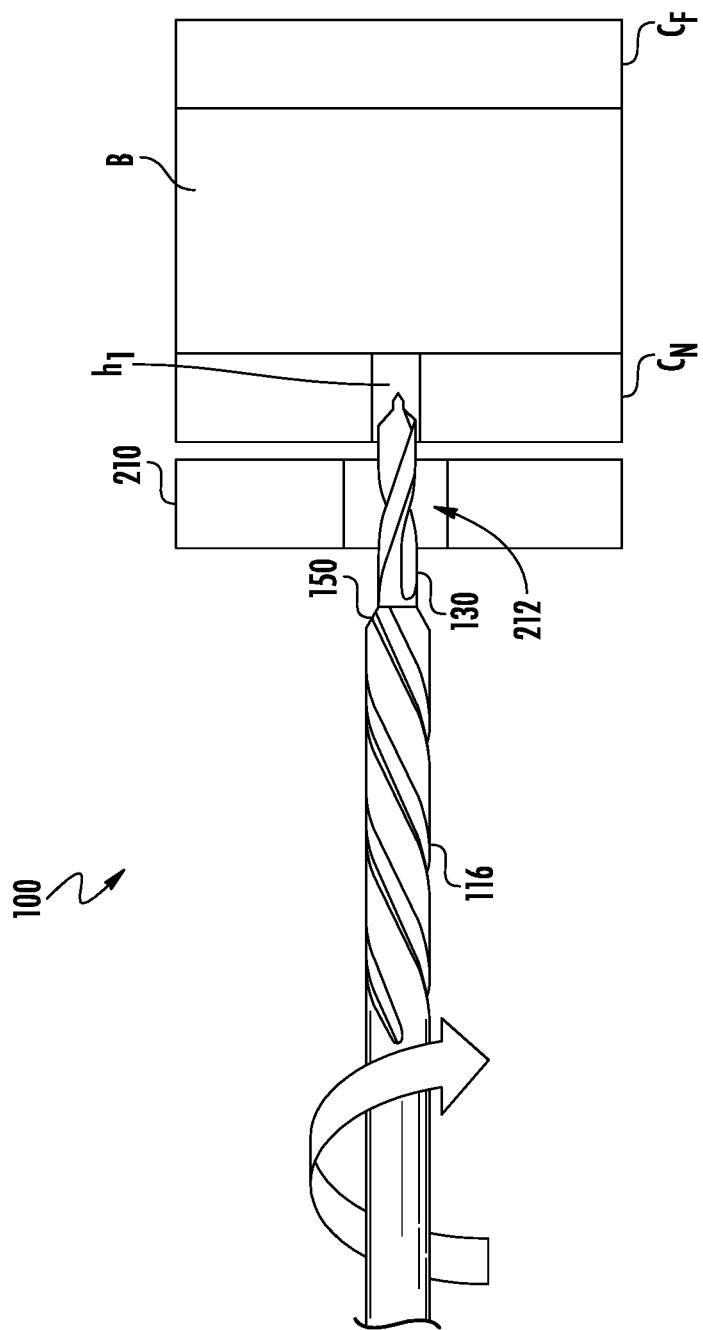
Figure 2C:
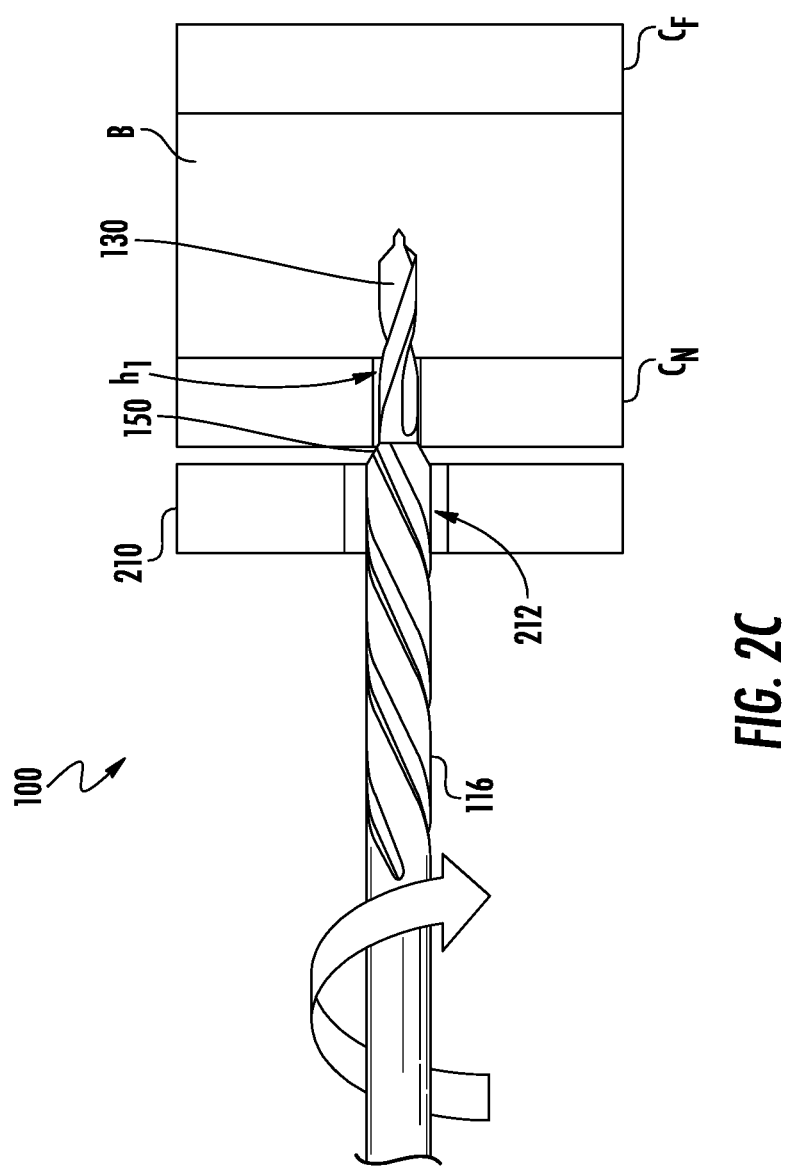

As illustrated in FIG. 2B, with the drill bit 100 rotating in the first direction (illustrated as clockwise direction), the distal cutting portion 130 is advanced through the patient's bone B thus forming a hole $h_1$ in the near cortex $C_n$ of the patient's bone B. Referring to FIG. 2C, the drill bit 100 is advanced through the patient's bone B until the shoulder 150 formed on the drill bit 100 contacts the near cortex $C_n$ of the patient's bone B. At this point, the drill bit 100 can no longer be advanced through the patient's bone B while rotating in the first direction. That is, contacting the near cortex $C_n$ of the patient's bone B with the shoulder 150 prevents further advancement of the drill bit 100 through the patient's bone B (e.g., the larger diameter proximal cutting portion 116 does not cut or advance because it is adapted and configured to cut/advance only when rotated in the second direction, which is opposite of the first direction). At this stage, a hole $h_1$ having a diameter of the distal cutting portion 130 is formed in the near cortex $C_n$ of the patient's bone B.

Figure 2D:
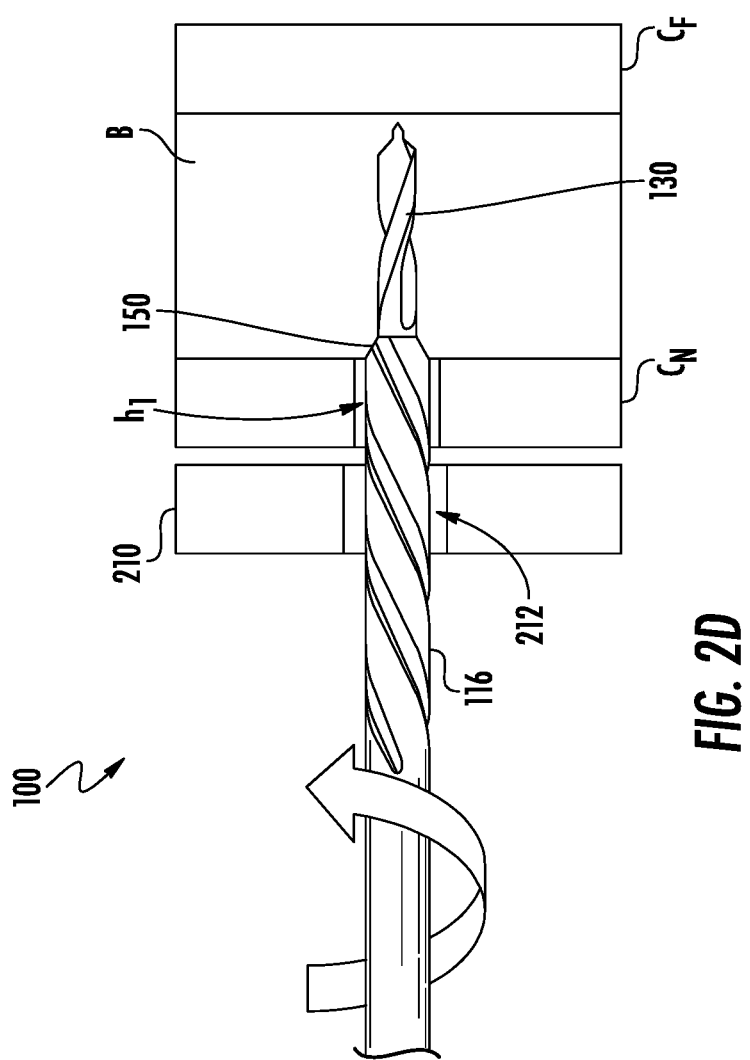

Referring to FIG. 2D, rotation of the drill bit 100 is reversed so that the drill bit 100 now rotates in the second direction (illustrated as counter-clockwise direction), with is opposite the initial first direction. With the drill bit 100 rotating in the second direction, the drill bit 100 is further advanced into the patient's bone B causing the larger diameter proximal cutting portion 116 to re-drill or enlarge the hole $h_1$ formed in the near cortex $C_n$.

Figure 2E:
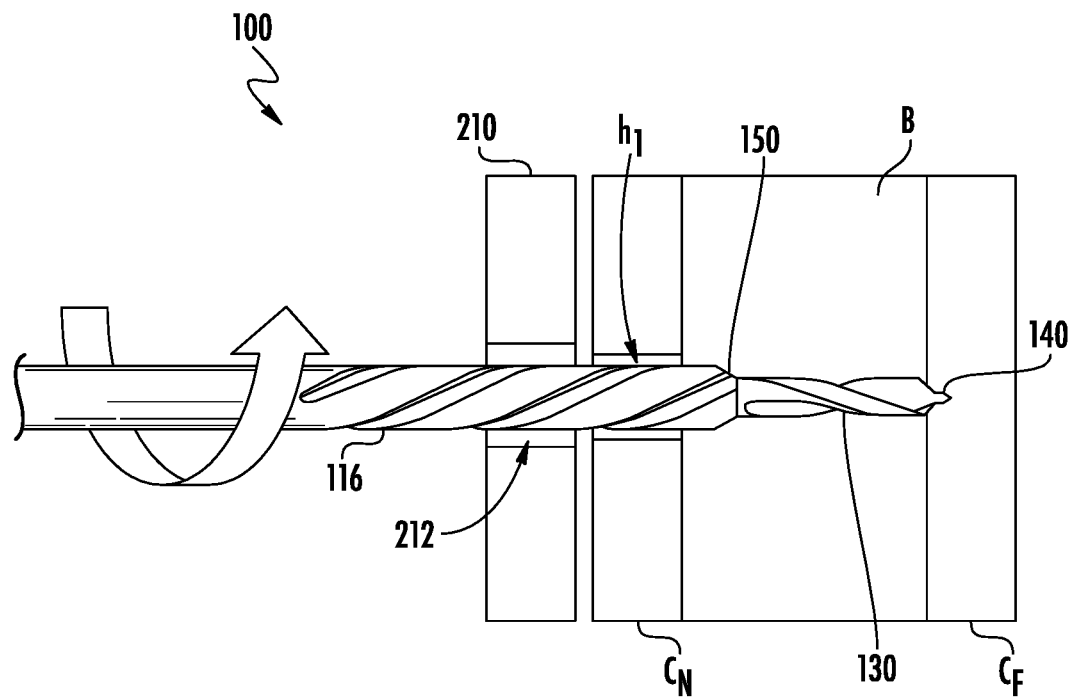

Referring to FIG. 2E, with the drill bit 100 rotating in the second direction, the drill bit 100 is advanced through the patient's bone B until the distal cutting portion 130 contacts the far cortex $C_f$ of the patient's bone B. At this point, the drill bit 100 can no longer be advanced through the patient's bone B while rotating in the second direction. That is, contacting the far cortex $C_f$ of the patient's bone B with the cutting tip 140 formed on the distal cutting portion 130 prevents further advancement of the drill bit 100 through the patient's bone B (e.g., the distal cutting portion 130 does not cut or advance because it is adapted and configured to cut/advance only when rotated in the first direction, which is opposite of the second direction).

Figure 2F:
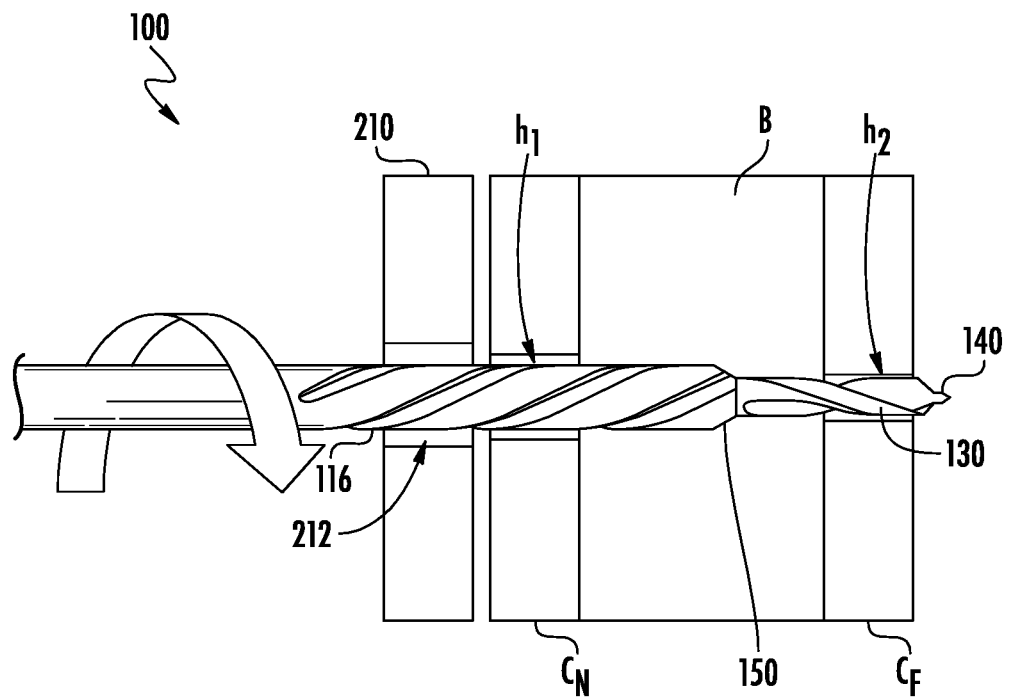

Referring to FIG. 2F, rotation of the drill bit 100 is reversed once again so that the drill bit 100 now rotates in the first direction (illustrated as clockwise direction). With the drill bit 100 rotating in the first direction, the drill bit 100 is further advanced into the patient's bone B causing the distal cutting portion 130 to form a hole $h_2$ in the far cortex $C_f$ of the patient's bone B.

Figure 2G:
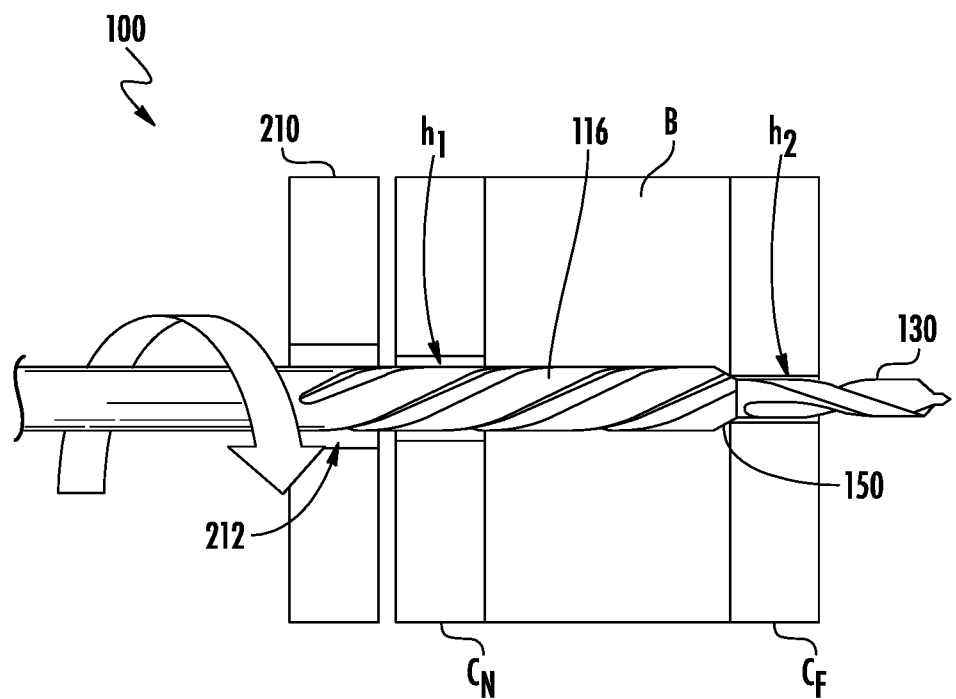

Referring to FIG. 2G, the drill bit 100 is advanced through the patient's bone B (e.g., the distal cutting portion 130 is cut or advanced through the far cortex $C_f$ of the patient's bone B) until the shoulder 150 formed on the drill bit 100 contacts the far cortex $C_f$ of the patient's bone B. At this point, the drill bit 100 can no longer be advanced through the patient's bone B while rotating in the first direction. That is, contacting the far cortex $C_f$ of the patient's bone B with the shoulder 150 prevents further advancement of the drill bit 100 through the patient's bone B (e.g., the larger diameter proximal cutting portion 116 does not cut or advance because it is adapted and configured to cut/advance only when rotated in the second direction, which is opposite of the first direction). As a result, risk of over-drilling the far cortex $C_f$ is eliminated or at least reduced.

Figure 2H:
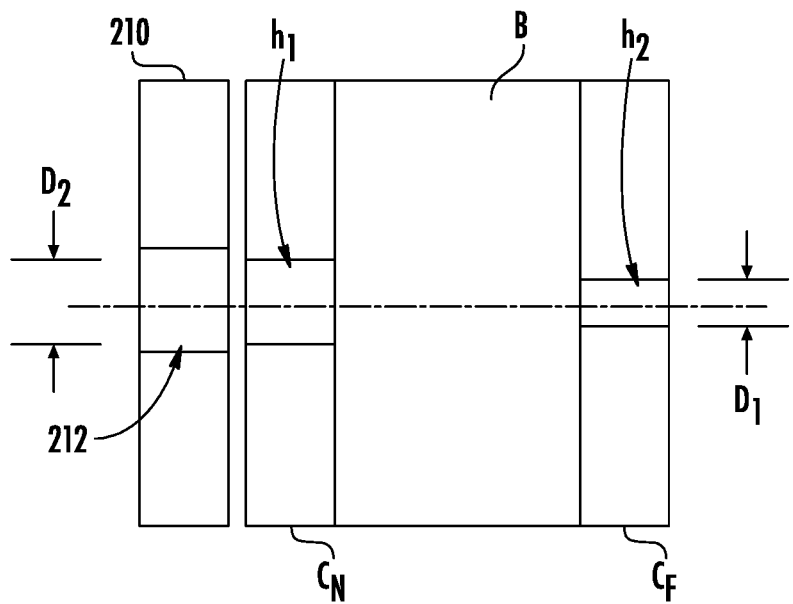

Referring to FIG. 2H, the drill bit 100 is removed. As a result, collinear holes $h_1$, $h_2$ are formed in the near and far cortex $C_n$, $C_f$, respectively, of the patient's bone B wherein the hole $h_1$ formed in the near cortex $C_n$ has a larger diameter equal to the diameter of the larger diameter proximal cutting portion 116 and the hole $h_2$ formed in the far cortex $C_f$ has a smaller diameter equal to the diameter of the distal cutting portion 130. The hole $h_2$ formed in the far cortex $C_f$ being sized and configured to receive a standard bone screw. The hole $h_1$ formed in the near cortex $C_n$ being adapted and configured to provide a gap or clearance with the shaft of the implanted bone screw so that a certain amount of flexibility is facilitated.

Thereafter, a bone plate 210 may be positioned adjacent to the near cortex $C_n$ of the patient's bone B and bone screws may be inserted through the openings 212 formed in the bone plate 210. The bone screws may be sized and configured to pass through the larger diameter hole $h_1$ formed in the near cortex $C_n$ of the patient's bone B and into the smaller diameter hole $h_2$ formed in the far cortex $C_f$ of the patient's bone B. As will be appreciated by one of ordinary skill, the larger diameter hole $h_1$ formed in the near cortex $C_n$ of the patient's bone B will enable controlled micro-motion of the bone plating system.

Referring to FIGS. 3A-3H, an example method of using the drill bit 100 in connection with implantation of an intramedullary nail (IM Nail) 310 will be described and illustrated. In one illustrated method of use, the drill bit 100 is utilized to form collinear holes in the near and far cortex $C_n$, $C_f$ of a patient's bone B. Additionally, the drill bit 100 is adapted and configured to prevent accidental over-drilling of the far cortex $C_f$.

As will be appreciated by one of ordinary skill in the art, an intramedullary nail 310 can be implanted into the intramedullary canal of a patient's bone. In one common procedure, a bone screw is inserted through a hole 312 formed in the IM Nail 310 to secure the position of the IM Nail 310 relative to the bone B.

Figure 3A:
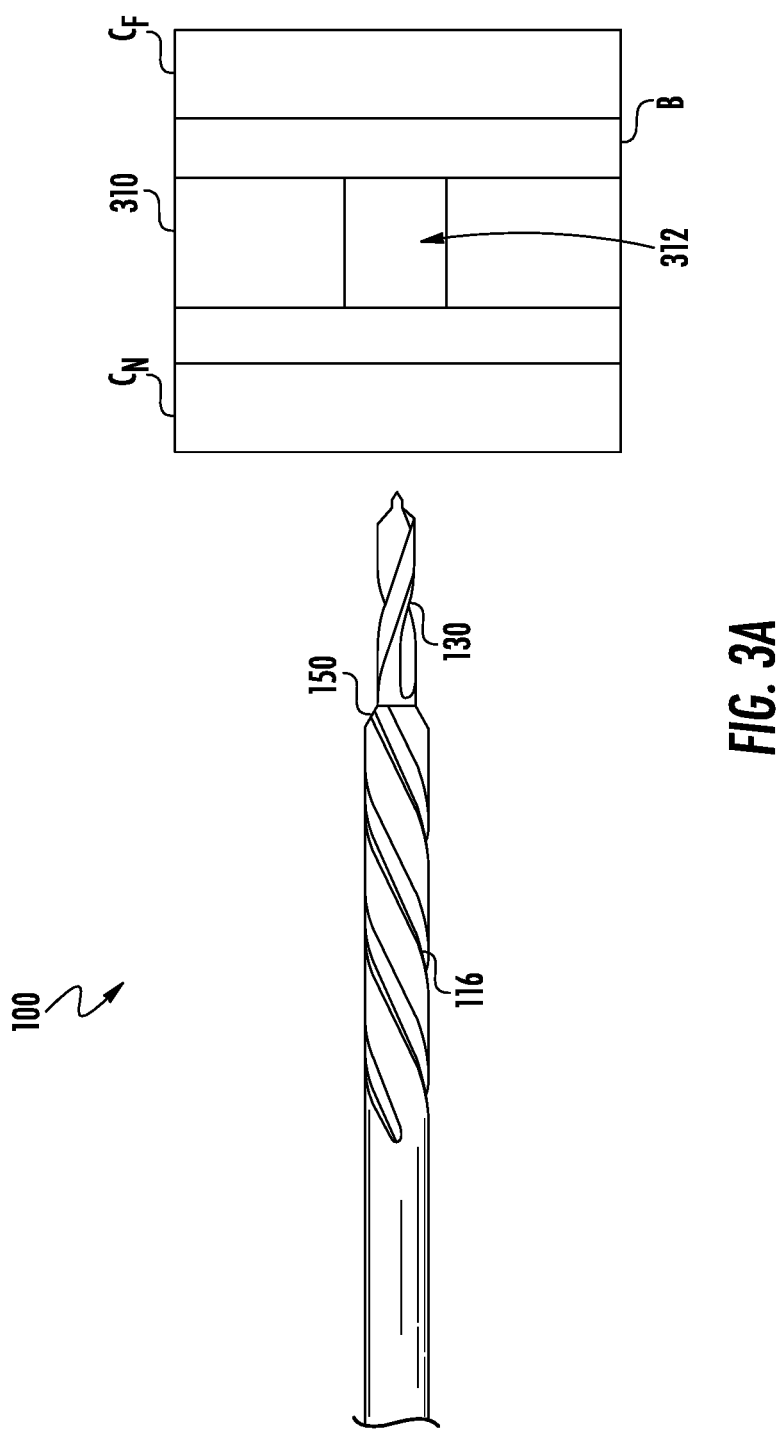
FIGS. 3A-3H shows a series of steps illustrating another example embodiment of a method for using the drill bit shown in FIG. 1.

As illustrated in FIG. 3A, the surgeon places the drill bit 100 adjacent to a targeted location in the patient's bone B. In use, as illustrated, the drill bit 100 can be, for example, aligned with and inserted through an opening 312 formed in the implanted IM Nail 310.

Figure 3B:
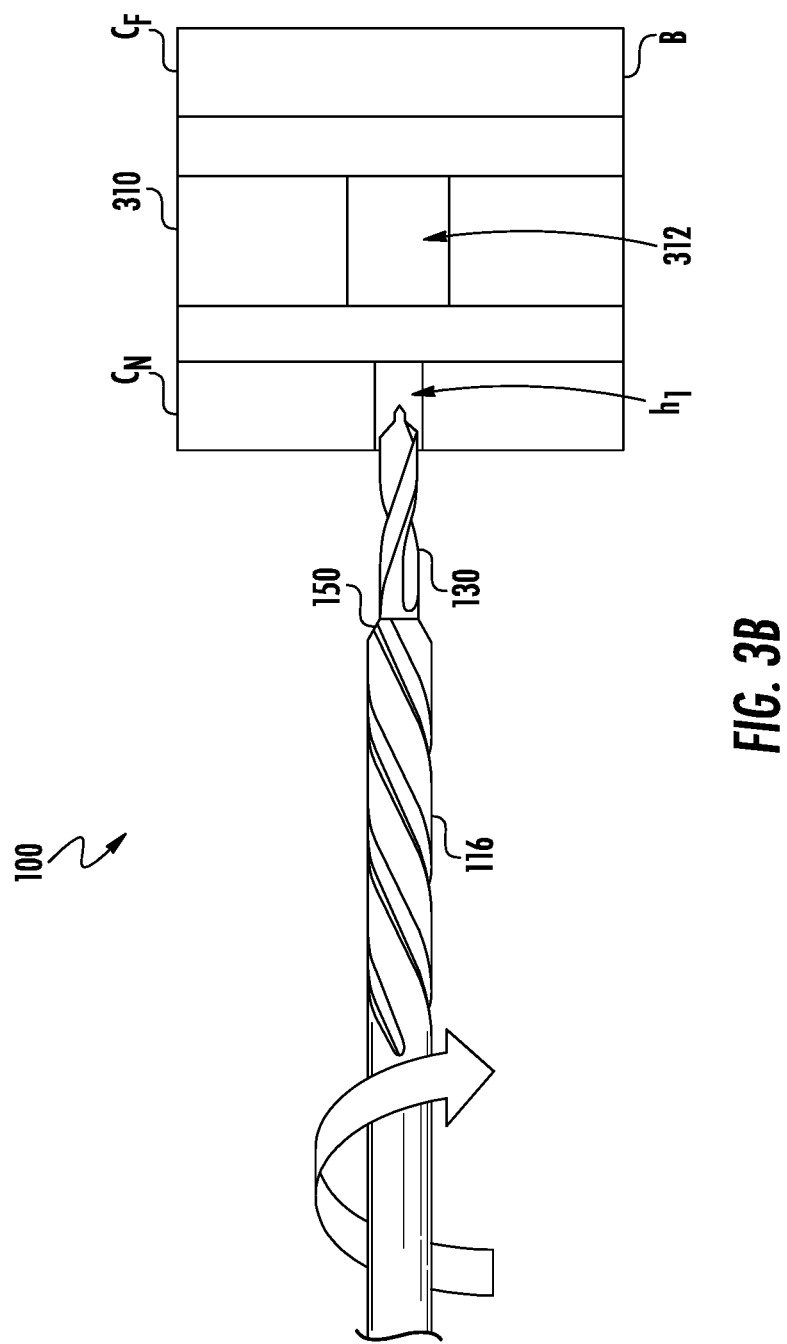
Figure 3C:
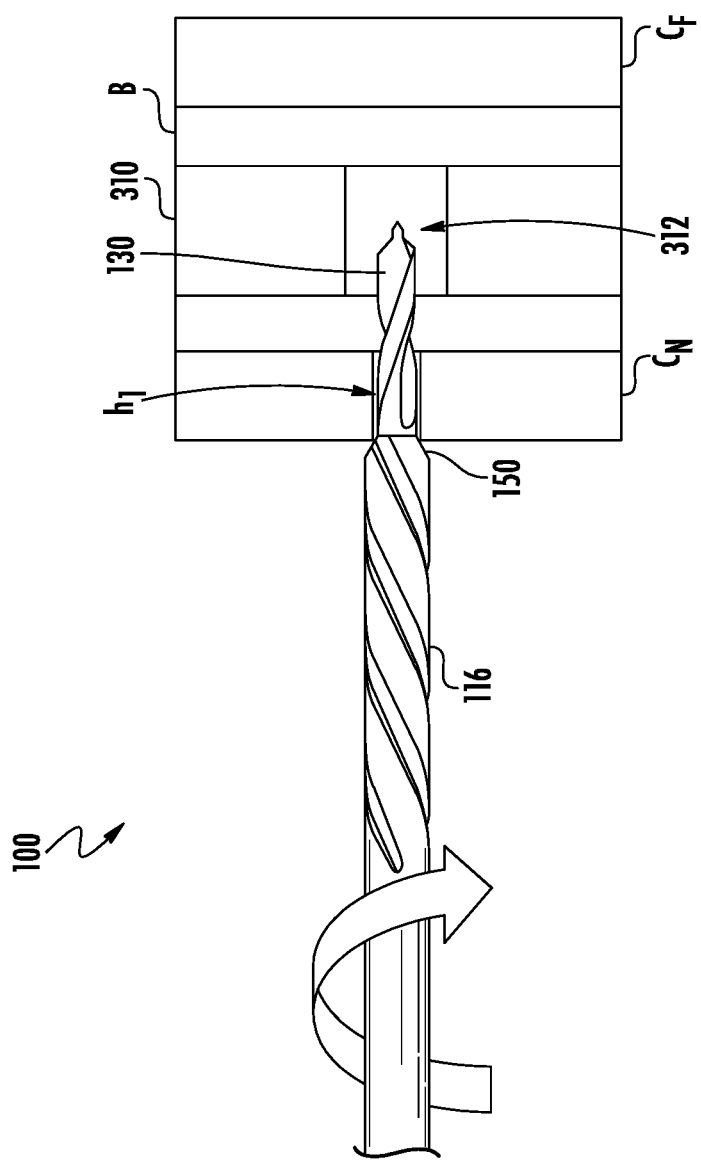

As illustrated in FIG. 3B, with the drill bit 100 rotating in the first direction (illustrated as clockwise direction), the distal cutting portion 130 is advanced through the patient's bone B thus forming a hole $h_1$ in the near cortex $C_n$ of the patient's bone B. Referring to FIG. 3C, the drill bit 100 is advanced through the patient's bone B until the shoulder 150 formed on the drill bit 100 contacts the near cortex $C_n$ of the patient's bone B. At this point, the drill bit 100 can no longer be advanced through the patient's bone B while rotating in the first direction. That is, contacting the near cortex $C_n$ of the patient's bone B with the shoulder 150 prevents further advancement of the drill bit 100 through the patient's bone B (e.g., the larger diameter proximal cutting portion 116 does not cut or advance because it is adapted and configured to cut/advance only when rotated in the second direction, which is opposite of the first direction). At this stage, a hole $h_1$ having a diameter of the distal cutting portion 130 is formed in the near cortex $C_n$ of the patient's bone B.

Figure 3D:
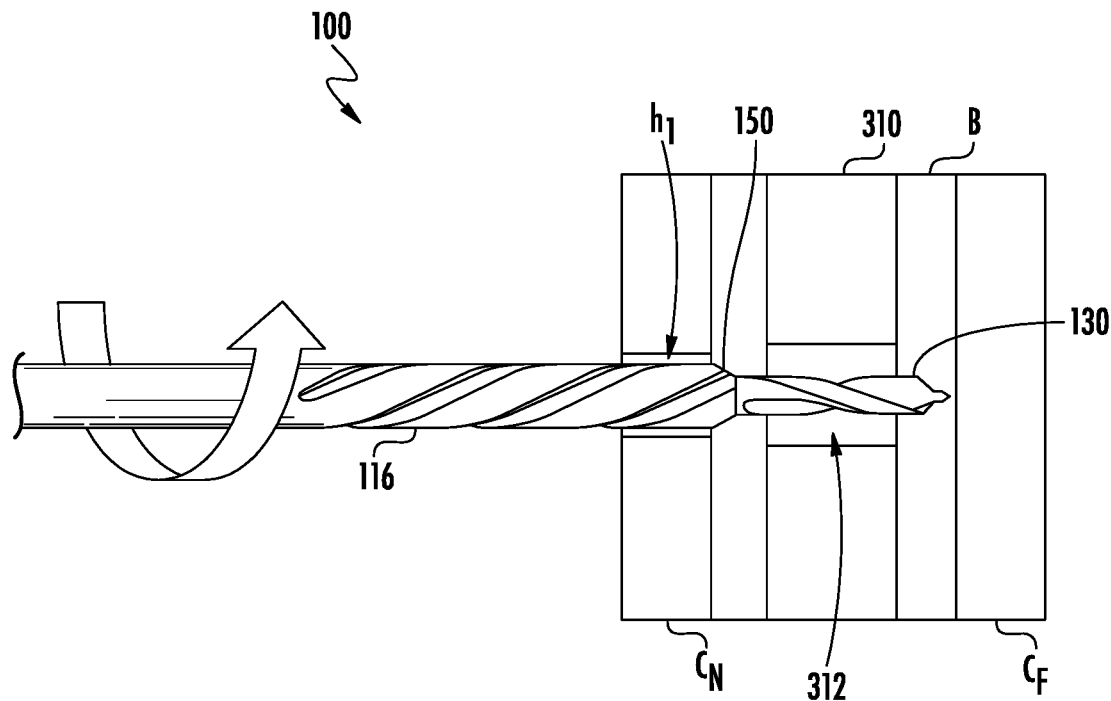

Referring to FIG. 3D, rotation of the drill bit 100 is reversed so that the drill bit 100 now rotates in the second direction (illustrated as counter-clockwise direction), which is opposite the initial first direction. With the drill bit 100 rotating in the second direction, the drill bit 100 is further advanced into the patient's bone B causing the larger diameter proximal cutting portion 116 to re-drill or enlarge the hole $h_1$ formed in the near cortex $C_n$.

Figure 3E:
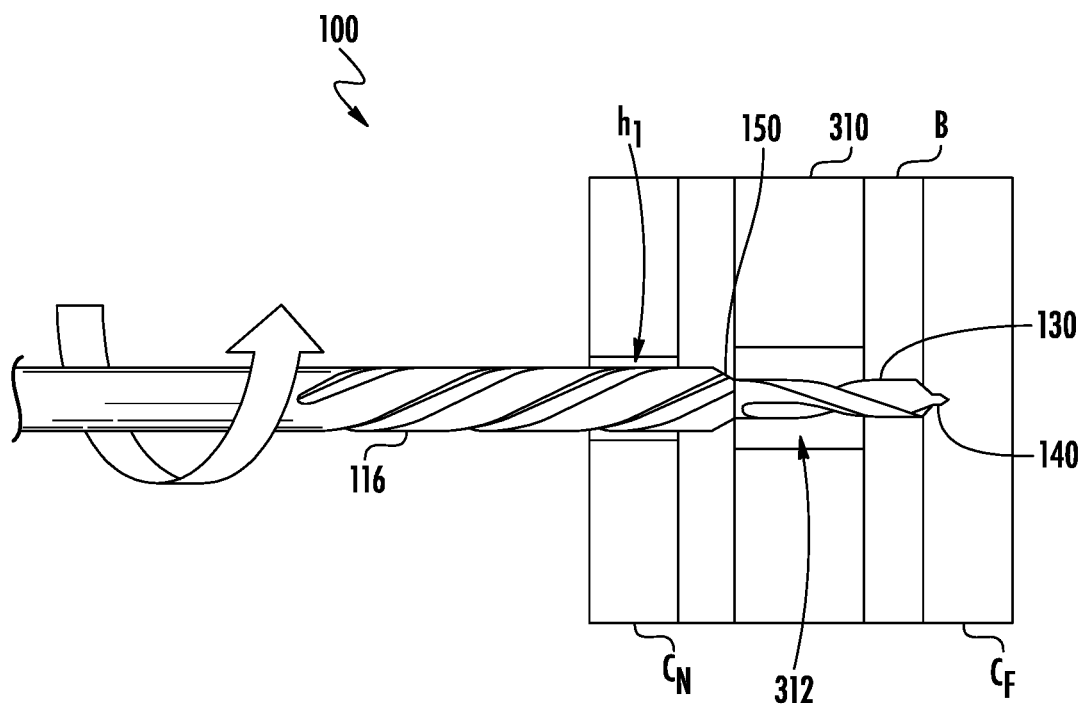

Referring to FIG. 3E, with the drill bit 100 rotating in the second direction, the drill bit 100 is advanced through the patient's bone B until the distal cutting portion 130 contacts the far cortex $C_f$ of the patient's bone B. At this point, the drill bit 100 can no longer be advanced through the patient's bone B while rotating in the second direction. That is, contacting the far cortex $C_f$ of the patient's bone B with the cutting tip 140 formed on the distal cutting portion 130 prevents further advancement of the drill bit 100 through the patient's bone B (e.g., the distal cutting portion 130 does not cut or advance because it is adapted and configured to cut/advance only when rotated in the first direction, which is opposite of the second direction).

Figure 3F:
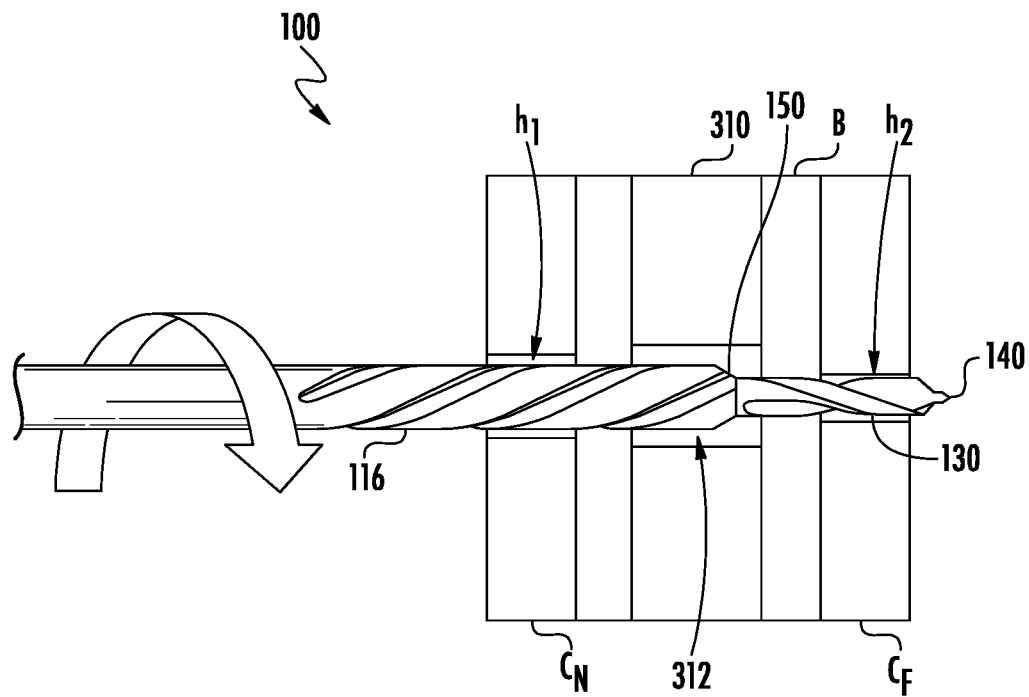

Referring to FIG. 3F, rotation of the drill bit 100 is reversed once again so that the drill bit 100 now rotates in the first direction (illustrated as clockwise direction). With the drill bit 100 rotating in the first direction, the drill bit 100 is further advanced into the patient's bone B causing the distal cutting portion 130 to form a hole $h_2$ in the far cortex $C_f$ of the patient's bone B.

Figure 3G:
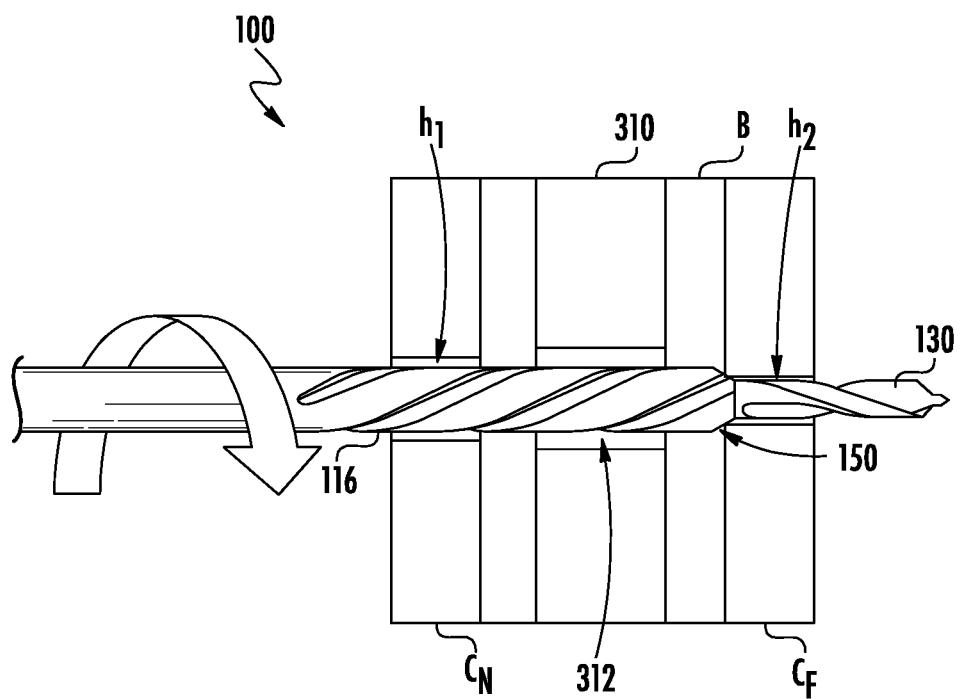

Referring to FIG. 3G, the drill bit 100 is advanced through the patient's bone B (e.g., the distal cutting portion 130 is cut or advanced through the far cortex $C_f$ of the patient's bone B) until the shoulder 150 formed on the drill bit 100 contacts the far cortex $C_f$ of the patient's bone B. At this point, the drill bit 100 can no longer be advanced through the patient's bone B while rotating in the first direction. That is, contacting the far cortex $C_f$ of the patient's bone B with the shoulder 150 prevents further advancement of the drill bit 100 through the patient's bone B (e.g., the larger diameter proximal cutting portion 116 does not cut or advance because it is adapted and configured to cut/advance only when rotated in the second direction, which is opposite of the first direction). As a result, risk of over-drilling the far cortex $C_f$ is eliminated or at least reduced.

Figure 3H:
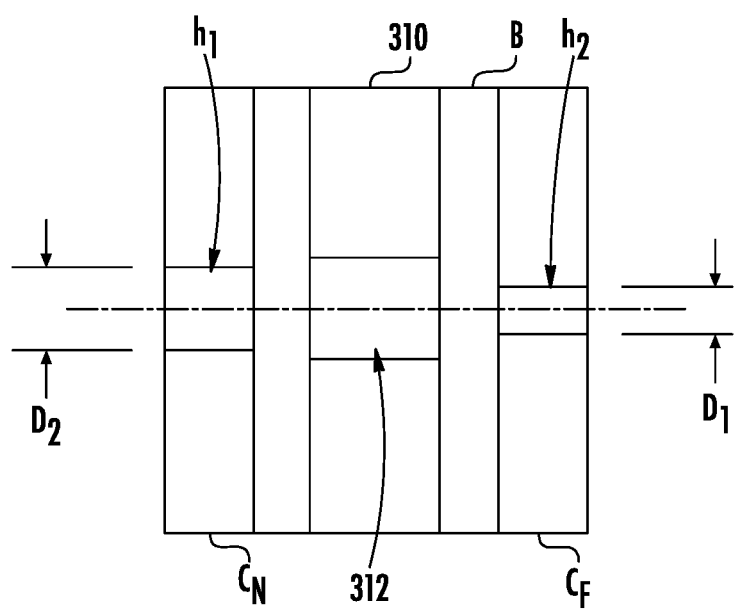

Referring to FIG. 3H, the drill bit 100 is removed. As a result, collinear holes $h_1$, $h_2$ are formed in the near and far cortex $C_n$, $C_f$, respectively, of the patient's bone B wherein the hole $h_1$ formed in the near cortex $C_n$ has a larger diameter equal to the diameter of the larger diameter proximal cutting portion 116 and the hole $h_2$ formed in the far cortex $C_f$ has a smaller diameter equal to the diameter of the distal cutting portion 130.

In use, by utilizing a stepped drill bit 100 in accordance with the present disclosure, a surgeon can prepare a larger diameter hole $h_1$ in the near cortex $C_n$ and a smaller diameter hole $h_2$ in the far cortex $C_f$ for receiving a bone screw without the necessity of removing the drill bit 100. As a result, collinearity of the holes $h_1$, $h_2$ formed in the near and far cortex $C_n$, $C_f$ is ensured. Additionally, the drill bit 100 is adapted and configured to prevent accidental over-drilling of the far cortex $C_f$. Finally, the drill bit 100 provides an easy to use apparatus and method that does not rely on any new implants or bone screws to provide controlled micro-motion.

In use, the drill bit 100 can be configured to advance through one of a plurality of through holes formed in the bone fixation implant as the hole is being formed in the anatomical structure or the drill bit 100 can form the hole prior to placement of the bone fixation implant. It should be appreciated, however, that the drill bit 100 can be configured to form or otherwise cut a hole into any anatomical structure.

In one example embodiment, the drill bit 100 can be integrally formed. That is, the body portion 110 and the distal cutting portion 130 can be integrally formed. Alternatively, the drill bit 100 could be made from multiple pieces that are then coupled together. The drill bit 100 can be made from any suitable material now known or hereafter developed including, for example, metal such as steel, titanium, or the like. The drill bit 100 can also be coated with a coating such as, for example, a titanium nitride coating, a diamond like carbon coating, a nickel coating, or the like.

In one embodiment, the drill bit 100 may have an overall length L1 of approximately 6 inches. The distal cutting portion 130 may have a length of approximately 0.7 inches.

The cutting portion 116 of the body portion 110 may extend approximately 1.4 inches from the distal end 112 of the body portion 110. In addition, the distal cutting portion 130 may include a first diameter of approximately 0.14 inches while the second diameter D2 may have a diameter of 0.22 inches.

In one embodiment, the surgical drill bit 100 may be provided as a stand-alone instrument. In other embodiments, a series of drill bits 100 can be provided in a kit. The kit including a number of different drill bits having varying lengths for the distal cutting portion, varying first and second diameters, etc. so that, in use, the surgeon can select the proper drill bit for the particular patient. Alternatively, referring to FIG. 4, in other embodiments, one or more drill bits 100 may be provided in a kit 400 including, for example, one or more bone fixation implants (illustrated as a bone plate) 210, one or more bone fixation elements such as, for example, bone screws 220, one or more drill guides (not shown), etc.

Figure 4:
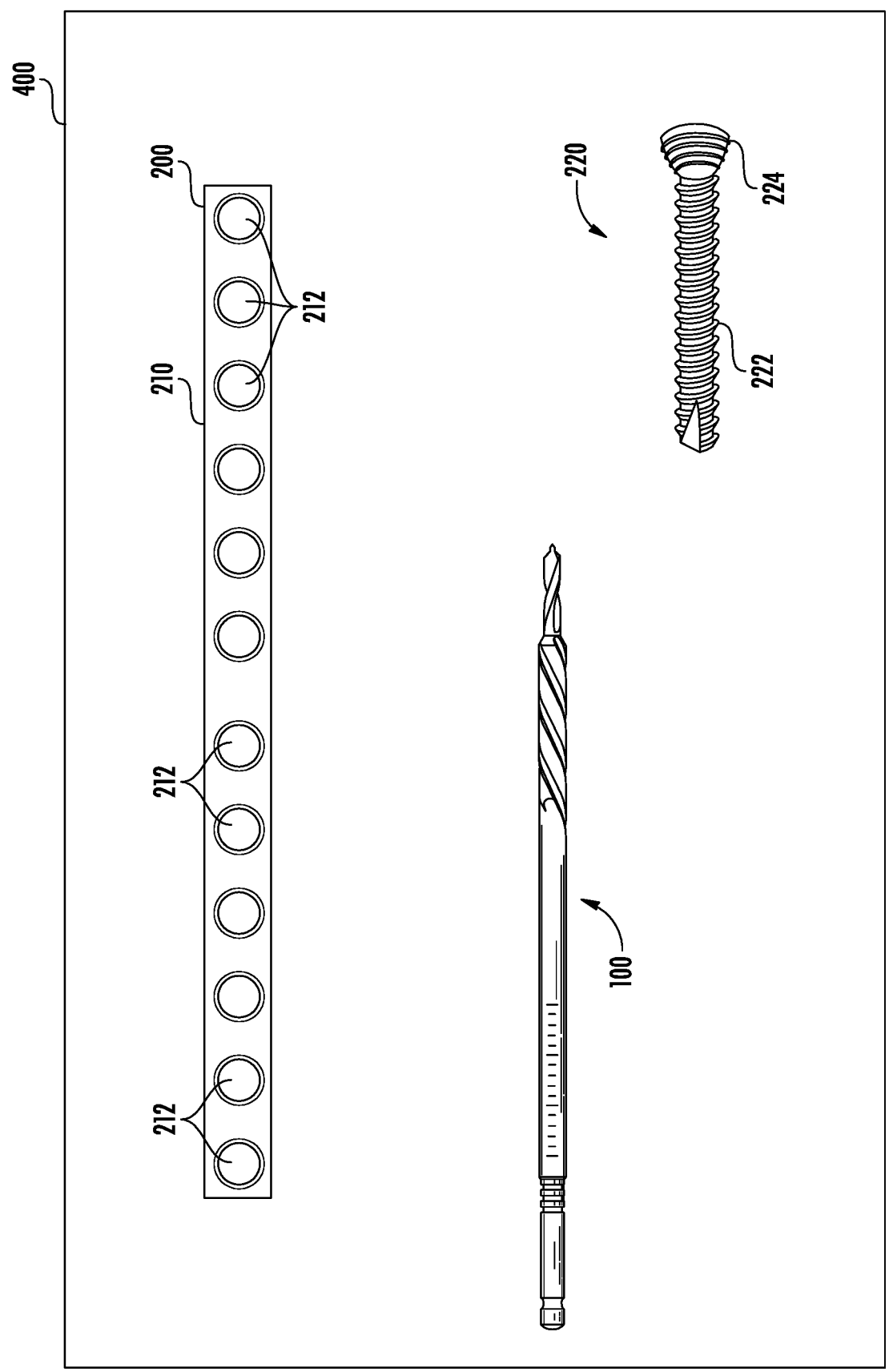
FIG. 4 is a schematically representation of an example embodiment of a kit incorporating, for example, the drill bit shown in FIG. 1.

In use, the bone fixation implant 200 and bone fixation elements 220 may be any orthopedic implant and/or fixation elements now known or hereafter developed. For example, the bone fixation element 220 may be in the form of bone screws 220 including a threaded shaft portion 222 and a threaded head portion 224. The bone fixation implant 220 may be, for example, a bone plate 210, an intramedullary nail 310, a humeral stem, or the like. As illustrated in FIG. 4, the bone fixation element 200 may be in the form of a bone plate 210 including a plurality of bone screw openings 212 extending through a thickness of the bone plate 210. The openings 212 being sized to receive the bone screws 220 therein to securely anchor the bone plate 210 to an underlying bone B. It should be appreciated that the bone plate 210 may be configured for use in association with any orthopedic surgery or procedure associated.

In one embodiment, the bone screw openings 212 may be threaded for threadably engaging the threaded head portion 224 of the bone screws 220. Alternatively, for example, the bone screw openings may include fins or projections (not shown) that extend radially inward from an inner surface of the bone screw openings and into the interior region of the openings, and which are configured to engage or cooperate with the threaded head portion 224 of the bone screws 220. In use, the fins engage the head portion 224 of the bone screw 220 in order to secure the bone screw 220 at a desired position and at a desired angular orientation within the bone screw opening relative to the bone plate. As described in U.S. Pat. No. 8,382,807 entitled Systems and Methods for Using Polyaxial Plates, the entire content of which is hereby incorporated by reference, the bone screw openings may be provided with a relatively jagged or undulating inner circumference formed by the inwardly protruding fins, and concavities or indentations are formed between adjacent pairs of the fins which extend to a location adjacent the inner surface of the opening. Additionally, the fins have a generally round configuration wherein the fins define convex protrusions extending inwardly into the openings. However, other shapes and configurations of the bone screw openings and/or the flexible fins are also contemplated.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. A method of forming first and second holes in a patient's bone, the method comprising:
    positioning a bone plate against the patient's bone, the bone including at least one opening for receiving a bone screw;
    forming a first hole in a first cortex of the patient's bone using a drill bit having a first diameter distal cutting portion;
    contacting the first cortex with a shoulder formed on the drill bit;
    reversing a direction of rotation of the drill bit;

enlarging the first hole formed in the first cortex of the patient's bone using a second diameter proximal cutting portion formed on the drill bit;

contacting a second cortex of the patient's bone with the first diameter distal cutting portion;

reversing the direction of rotation of the drill bit;

forming a second hole in the second cortex of the patient's bone using the first diameter distal cutting portion of the drill bit; and inserting a bone screw through the at least one opening formed in the bone plate and into the first and second holes formed in the patient's bone to secure the bone plate to the patient's bone.

2. The method of claim 1, wherein the second diameter proximal cutting portion has a larger diameter than the first diameter distal cutting portion.

3. The method of claim 1, wherein the first hole formed in the first cortex is collinear with the second hole formed in the second cortex.

4. The method of claim 1, wherein the bone screw has a diameter arranged and configured to engage the second hole formed in the second cortex of the patient's bone, the bone screw being arranged and configured to provide micromotion relative to the first hole formed in the first cortex.

5. The method of claim 4, wherein the diameter of the bone screw is less than the second diameter proximal cutting portion formed on the drill bit so that the diameter of the bone screw is less than the diameter of the first hole formed in the first cortex.

6. A method of forming first and second holes in a patient's bone, the method comprising:

positioning an intramedullary nail into the patient's bone, the intramedullary nail including at least one opening for receiving a bone screw;

forming a first hole in a first cortex of the patient's bone using a drill bit having a first diameter distal cutting portion;

contacting the first cortex with a shoulder formed on the drill bit;

reversing a direction of rotation of the drill bit;

enlarging the first hole formed in the first cortex of the patient's bone using a second diameter proximal cutting portion formed on the drill bit;

contacting a second cortex of the patient's bone with the first diameter distal cutting portion;

reversing the direction of rotation of the drill bit;

forming a second hole in the second cortex of the patient's bone using the first diameter distal cutting portion of the drill bit; and inserting a bone screw through the first hole formed in the first cortex, through the at least one opening formed in the intramedullary nail, and into the second hole formed in the second cortex to secure the intramedullary nail to the patient's bone.

7. The method of claim 6, wherein the bone screw has a diameter arranged and configured to engage the second hole formed in the second cortex of the patient's bone, the bone screw being arranged and configured to provide micromotion relative to the first hole formed in the first cortex.

8. The method of claim 7, wherein the diameter of the bone screw is less than the second diameter proximal cutting portion formed on the drill bit so that the diameter of the bone screw is less than the diameter of the first hole formed in the first cortex.

9. The method of claim 6, wherein the second diameter proximal cutting portion has a larger diameter than the first diameter distal cutting portion.

10. The method of claim 6, wherein the first hole formed in the first cortex is collinear with the second hole formed in the second cortex.

\* \* \* \* \*